(12) United States Patent
Luo

(10) Patent No.: US 12,214,134 B2
(45) Date of Patent: Feb. 4, 2025

(54) ORAL AND NASAL SEALING INTERFACE PAD

(71) Applicant: DCSTAR INC, New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 18/324,259

(22) Filed: May 26, 2023

(65) Prior Publication Data

US 2024/0390626 A1 Nov. 28, 2024

(51) Int. Cl.
*A61M 16/06* (2006.01)
(52) U.S. Cl.
CPC . *A61M 16/0616* (2014.02); *A61M 2210/0618* (2013.01); *A61M 2210/0625* (2013.01)
(58) Field of Classification Search
CPC .............. A61M 16/06; A61M 16/0605; A61M 16/0611; A61M 16/0616; A61M 16/0622; A61M 16/0666; A61M 2016/0661; A61M 2210/0618; A61M 2210/0625
See application file for complete search history.

(56) References Cited

U.S. PATENT DOCUMENTS

| | | | | |
|---|---|---|---|---|
| 2018/0256844 | A1* | 9/2018 | Galgali | A61M 16/0616 |
| 2020/0054850 | A1* | 2/2020 | Davidson | A61M 16/0816 |
| 2021/0038848 | A1* | 2/2021 | Eves | A61M 16/0605 |
| 2022/0280738 | A1* | 9/2022 | Bearne | A61M 16/0611 |
| 2023/0218848 | A1* | 7/2023 | Scheiner | A61M 16/0875 |
| | | | | 128/205.25 |

FOREIGN PATENT DOCUMENTS

WO WO-2022061401 A1 * 3/2022

\* cited by examiner

*Primary Examiner* — Joseph D. Boecker
*Assistant Examiner* — Brian T Khong
(74) *Attorney, Agent, or Firm* — HSML P.C.

(57) ABSTRACT

An oral and nasal sealing interface pad including a rigid part and a lining pad. The rigid part has a circular opening on one side and a joint part on the other side; the lining pad is fixedly connected to the joint part and is located below the user's nose. The lining pad includes a nasal area corresponding to and abutting the user's nasal tip and a mouth area corresponding to and surrounding the user's mouth. The space enclosed by the nasal area is connected to the space enclosed by the mouth area, together forming an integrated respiratory chamber. The nasal area includes a nasal tip area and an alar area. The nasal tip area has at least one thin area for accommodating the user's nasal tip, and the nasal tip area is equipped with a first wing for abutting against the user's columella.

19 Claims, 8 Drawing Sheets

ORAL AND NASAL SEALING INTERFACE PAD

TECHNICAL FIELD

The present disclosure relates to interface devices for delivering respiratory airflow to patients, specifically to an oral and nasal sealing interface pad for use under a patient's nose.

BACKGROUND

Obstructive sleep apnea is a sleep-related breathing disorder caused by relaxation of the muscles in the tongue, soft palate, and the posterior wall of the oropharynx during sleep. It usually causes the patient to stop breathing for 10 seconds or more each time, with this situation occurring 5-30 times or more per hour. The persistence of this condition can lead to excessive daytime sleepiness, snoring at night, morning headaches, and possible complications such as cardiovascular diseases and brain damage. Continuous positive airway pressure ventilation is a common treatment for obstructive sleep apnea, which involves delivering pressurized air to the patient's airway through a breathing machine and air delivery tube to open the airway and restore normal breathing. During treatment, patients wear masks to maintain a seal and avoid affecting treatment outcomes. Currently, there are three main types of masks on the market, including full-face masks covering the patient's nose and mouth, nasal masks, and nasal pillows. Full-face masks are suitable for mouth-breathing patients, but they are large and heavy, making it inconvenient to wear glasses, and some patients find them unattractive. Nasal masks only cover the patient's nose and seal along the upper lip and nose bridge areas. They have a smaller contact area with the face, making it more convenient for patients to wear glasses, read, and watch television while wearing the mask. However, for patients with a habit of mouth breathing, this can cause dry mouth and noise. Nasal pillows are nasal plugs placed inside the patient's nostrils, and some patients find that they put pressure on the nose.

In recent years, a new type of nasal and oral mask that achieves a sealing effect around the patient's nose and mouth has appeared on the market. This mask can cover both the nose and mouth, reducing contact with the face, making the product lighter and having less impact on the patient's daily life. However, this type of nasal and oral mask uses a separate design for the nose and mouth areas, with openings for the nose and mouth separated by the strap. The purpose of the strap is to support the mask and prevent it from deforming and collapsing. At the same time, the presence of the strap will have a certain impact on the mask's ability to deform. The human nose has distinct curves on both sides, and the mask cannot conform to the curvature of the alae or nasal base, affecting the mask's seal. Secondly, from a production process perspective, the strap connecting the nose and mouth areas increase production difficulty. During the molding process, the mask produced by injection molding must be removed from the mold. Due to the presence of strap, the mask must have enough stretch to remove the mold stuck in the mask chamber. This not only increases production difficulty but may also cause the mask to stretch and break, increasing the defect rate. Furthermore, masks with strap are not convenient to wear and require a cumbersome adjustment process. Since the strap position of the nose and mouth areas corresponds to the position of the philtrum, some masks even divide the nose area so that the strap correspond to the nostrils on both sides. In this case, when wearing the mask, the user needs to align the mask strap to the appropriate position; otherwise, there is a high probability of air leakage or discomfort. Additionally, due to the user's face being prone to oil and sweat when wearing the mask, the mask may shift during airflow pressure or user movement, affecting the mask's sealing.

SUMMARY

Based on this, it is necessary to address the above shortcomings and provide an oral and nasal sealing interface pad that has a good fit with the user's face, is easy to process and wear, and has good sealing properties.

An oral and nasal sealing interface pad, configured to provide positive pressure breathing gas to the user's airway, includes:
  a rigid part, one side of which has a circular opening for accessing positive pressure breathing gas, and another side has a joint part; and
  a lining pad, which is fixedly connected to the joint part and constructed to be located below the user's nose for delivering positive pressure breathing gas to the user's mouth and nasal airways, the lining pad including a nasal area corresponding to and configured to abut the user's nasal tip and a mouth area corresponding to and surrounding the user's mouth, the space enclosed by the nasal area communicating with the space enclosed by the mouth area and together forming an integrated respiratory chamber;
  the nasal area includes a nasal tip area and an alar area on both sides, e.g., two sides, of the nasal tip area, the nasal tip area having at least one thin area for accommodating the user's nasal tip and having a first wing for abutting the user's nasal columella, the alar area having at least one non-thin area 38.

In one embodiment, the non-thin area 38 of the alar area has ribs or multi-layer walls, the thickness of the ribs being greater than or equal to 0.3 mm.

In one embodiment, the space enclosed by the nasal area is an M-shaped structure or a heart-shaped structure.

In one embodiment, the first wing separates the alar area on both sides to form a first opening and a second opening, the distance between the first opening and the second opening being at most 30 mm.

In one embodiment, both sides of the alar area have a second wing for fitting the user's nose base, the straight-line distance between the second wings on both sides is at or between 10-15 mm, and the straight-line distance between the second wings on both sides is less than the distance between the first opening and the second opening.

The disclosure also discloses an oral and nasal sealing interface pad, configured to provide positive pressure breathing gas to the user's airway, including:
  a rigid part, one side of which has a circular opening for accessing positive pressure breathing gas, and the other side has a joint part; and
  a lining pad, which is fixedly connected to the joint part and constructed to be located below the user's nose for delivering positive pressure breathing gas to the user's mouth and nasal airways, the lining pad including a nasal area corresponding to and abutting the user's nasal tip and a mouth area corresponding to and surrounding the user's mouth, the space enclosed by the nasal area communicating with the space enclosed by the mouth area and together forming an integrated respiratory chamber;

the nasal area includes a nasal tip area and an alar area on both sides of the nasal tip area, the nasal tip area has at least one thin area for accommodating the user's nasal tip, and the nasal tip area has a first wing for abutting the user's nasal columella;

the first wing has at least one of the following features:

the length of the first wing is at or between 2-20 mm;

the width of the first wing is at or between 2-20 mm;

the thickness of the first wing is at or between 0.3-1.2 mm; and when the axial direction of the circular opening of the rigid part is parallel to the horizontal line, the angle α between the first wing and the horizontal line is at or between 0-90°.

In one embodiment, when the axial direction of the circular opening of the rigid part is parallel to the horizontal line, the first wing is parallel to the horizontal line.

In one embodiment, the shape of the first wing is adapted to the shape of the user's nasal columella; the vertical cross-section where the first wing connects to the nasal tip area is an L-shaped structure.

In one embodiment, the first wing can swing relative to the nasal tip area.

The disclosure also discloses an oral and nasal sealing interface pad, configured to provide positive pressure breathing gas to the user's airway, the oral and nasal sealing interface pad including:

a rigid part, one side of which has a circular opening for accessing positive pressure breathing gas, and the other side has a joint part; and a lining pad, which is fixedly connected to the joint part and constructed to be located below the user's nose for delivering positive pressure breathing gas to the user's mouth and nasal airways, the lining pad including a nasal area corresponding to and configured to abut the user's nasal tip and a mouth area corresponding to and surrounding the user's mouth, the space enclosed by the nasal area communicating with the space enclosed by the mouth area and together forming an integrated respiratory chamber;

the nasal area includes a nasal tip area and an alar area on both sides of the nasal tip area, the nasal tip area having at least one thin area for accommodating the user's nasal tip and having a first wing for abutting the user's nasal columella, the friction coefficient of the outer surface of the first wing being greater than the friction coefficient of the other parts of the nasal area.

In one embodiment, the mouth area includes a chin area and cheek areas, with the friction coefficient of the chin area being greater than that of the cheek areas.

The disclosure also discloses an oral and nasal sealing interface pad, configured to provide positive pressure breathing gas to the user's airway, the oral and nasal sealing interface pad including:

a rigid part, one side of which has a circular opening for accessing positive pressure breathing gas, and another side has a joint part; and a lining pad, which is fixedly connected to the joint part and constructed to be located below the user's nose for delivering positive pressure breathing gas to the user's mouth and nasal airways, the lining pad including a nasal area corresponding to and configured to abut the user's nasal tip and a mouth area corresponding to and surrounding the user's mouth, the space enclosed by the nasal area communicating with the space enclosed by the mouth area and together forming an integrated respiratory chamber;

the nasal area includes a nasal tip area and an alar area on both sides of the nasal tip area, the nasal tip area having at least one thin area for accommodating the user's nasal tip, with a thickness at or between 0.3-1.2 mm, and a thickness ratio between the thin area and the adjacent non-thin area 38 at or between 0.05-0.8.

In one embodiment, the spring constant of the thin area is greater than that of the adjacent non-thin area 38.

In one embodiment, the hardness of the rigid part is greater than the hardness of the lining pad, which is made of silicone material, and the edge of the lining pad has an arcuate portion.

In one embodiment, the lining pad is integrally formed and has a single-layer wall structure or a multi-layer wall structure.

The oral and nasal sealing interface pad of the present disclosure has at least the following beneficial effects:

Eliminating the strap connecting the nasal area and the mouth area to connect the spaces enclosed by the nose and mouth areas to form an integrated respiratory chamber provides greater deformation space for the alar area on both sides to adapt to the user's alae and nasal base curvature. And the removal of the strap is beneficial for the sides of the mask to fit the facial contours under the effect of treatment pressure; The non-thin area 38 setting in the alar area ensures that the interface pad is securely sealed with the face while effectively preventing the alar area from deforming outward.

By eliminating the strap connecting the nose and mouth areas of the interface pad, the side of the interface pad facing the user's face has only one opening (the space enclosed by the nose area is connected to the space enclosed by the mouth area). This larger opening is advantageous for removing the mold from the interface pad during the manufacturing process. Moreover, the removal of the strap not only achieves good sealing performance, but also simplifies the product structure, facilitates production, improves efficiency, and reduces costs.

The interface pad is worn from bottom to top, allowing the nasal tip to fit perfectly with the pad's nasal tip area, only needing to accommodate the nose and mouth in a single respiratory chamber. Thus, there is no need for complicated adjustments to position the nose and mouth within their corresponding areas, making it easier to wear the interface pad and reducing the difficulty of wearing it.

By increasing the friction coefficient of the outer surface of the first wing, the friction force between the first wing and the skin is increased, preventing displacement during wear due to air pressure or user movement, ensuring the sealing of the interface pad during use.

DETAILED DESCRIPTION

Figure 1:
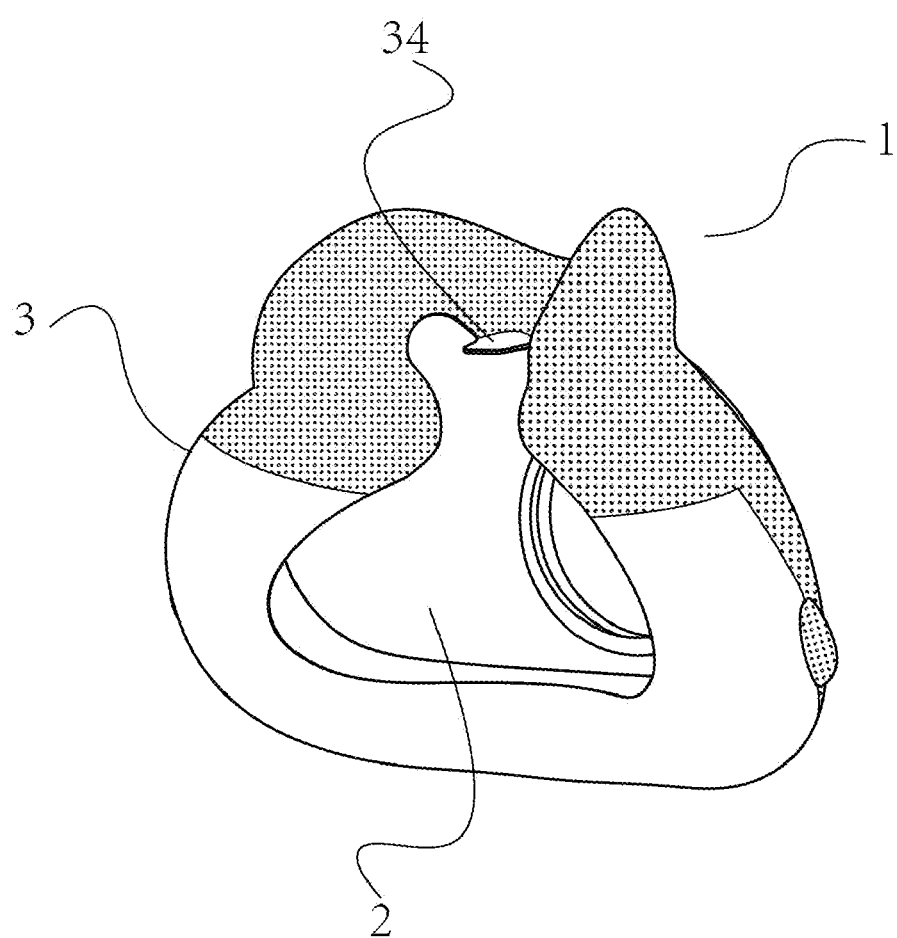
FIG. 1 is a schematic diagram of the structure of an oral and nasal sealing interface pad in an embodiment of the present disclosure.

In order to make the objectives, features, and advantages of the present disclosure more apparent and easy to understand, a detailed description of specific embodiments of the present disclosure is provided below in conjunction with the accompanying drawings. Many specific details are set forth in the following description in order to provide a thorough understanding of the present disclosure. However, the present disclosure can be implemented in many other ways different from those described here, and those skilled in the art can make similar improvements without departing from the spirit of the present disclosure. Therefore, the present disclosure is not limited by the specific embodiments disclosed below.

The present disclosure discloses an oral and nasal sealing interface pad that is easy to process and wear and has good facial fit and sealing performance, designed to seal around the user's nose and mouth without touching the bridge of the nose, covering the airway entrance of the user's nose and mouth, thereby delivering the breathing gas flow in a non-invasive manner through the user's nasal and oral chamber to the patient's airway.

Referring to FIGS. 1-4, the oral and nasal sealing interface pad 1 is configured to provide positive pressure breathing gas to the user's airway. The pad 1 includes a rigid part 2 and a lining pad 3, made of different materials. In addition, the hardness of the rigid part 2 is greater than that of the lining pad 3. In this way, the rigid part 2 with higher hardness can provide support for the lining pad 3 and prevent the difficulty in connecting the oral and nasal sealing interface pad 1 with external breathing equipment due to deformation of the rigid part 2. The lower hardness of the lining pad 3 can generate a certain deformation to fit the user's face, avoiding air leakage during use, and reducing the pressure and injury caused by the oral and nasal sealing interface pad 1 on the user's face. Preferably, in this embodiment, the rigid part 2 is made of hard plastic materials such as Polycarbonate, Acrylonitrile Butadiene Styrene, Polyamide, and Polyvinyl Chloride to ensure the hardness of the rigid part 2; the lining pad 3 is made of silicone material to provide sufficient deformation ability to fit the user's facial contour. Additionally, the pad 3 may also be made of an elastic material that deforms under pressure, such as rubber, thermoplastic elastomer, or silicone resin material, with a hardness range at or between Shore A10-Shore A60.

One side of the rigid part 2 is provided with a circular opening 21 for accessing positive pressure breathing gas, which is used to access continuous positive airway pressure equipment breathing gas. A frame part can also be accommodated in the circular opening 21 as a connector for connecting to external breathing equipment. The other side of the rigid part 2 is provided with a joint part 22, which provides a connection and support location for the lining pad 3. In this embodiment, the rigid part 2 and the lining pad 3 are permanently attached, formed as a unit by injection molding or by adhesive bonding.

Figure 7:
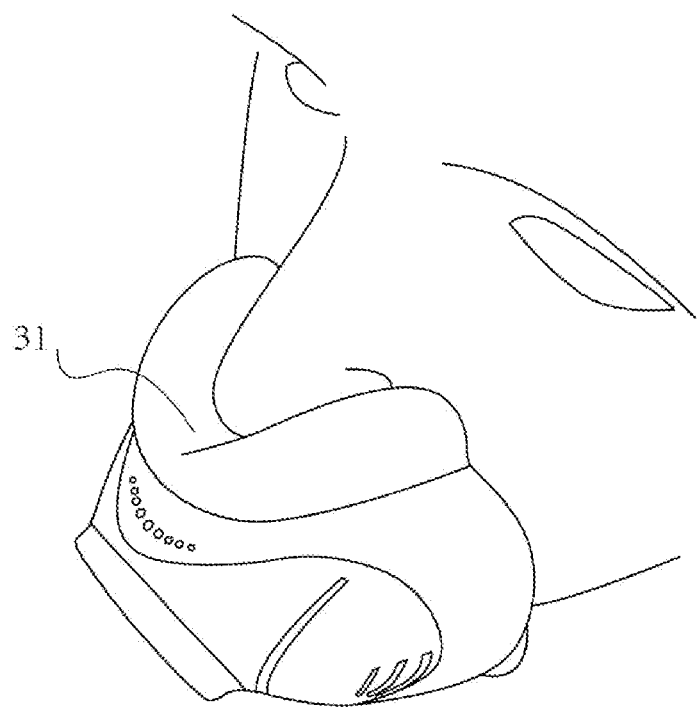
FIG. 7 is a schematic diagram of the structure of an oral and nasal sealing interface pad when worn in an embodiment of the present disclosure.
Figure 8:
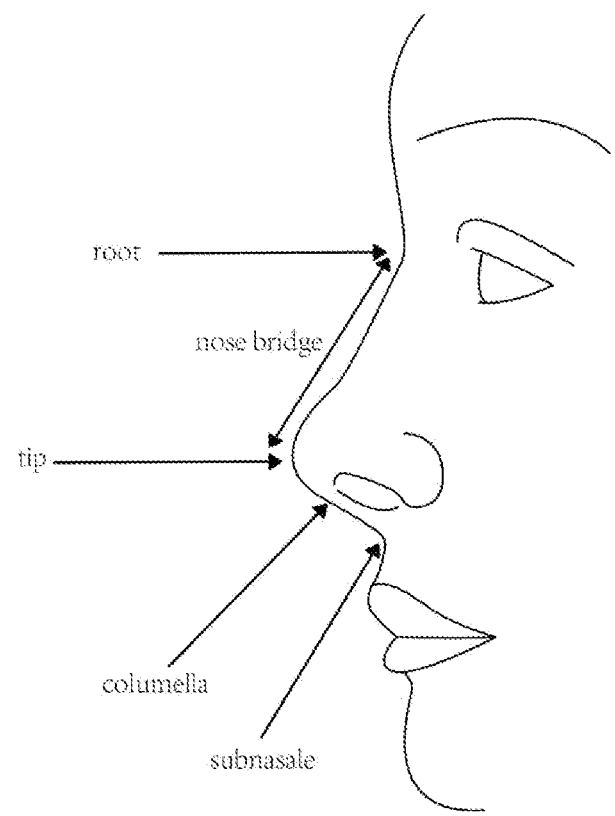
FIG. 8 is a schematic diagram of the facial names of the user.

Referring to FIG. 7, the lining pad 3 is fixedly connected to the joint part 22 of the rigid part 2 and is configured to be located below the user's nose to deliver positive pressure breathing gas to the user's oral and nasal airways. In this embodiment, the lining pad 3 is used to directly contact the user's face and form a seal when the oral and nasal sealing interface pad is in use, providing a soft contact point, avoiding injury to the user's face caused by the oral and nasal sealing interface pad 1, and the lining pad 3 is configured to be located below the user's nose to fully expose the user's nose bridge, reducing the contact area between the interface pad and the user's face.

Figure 2:
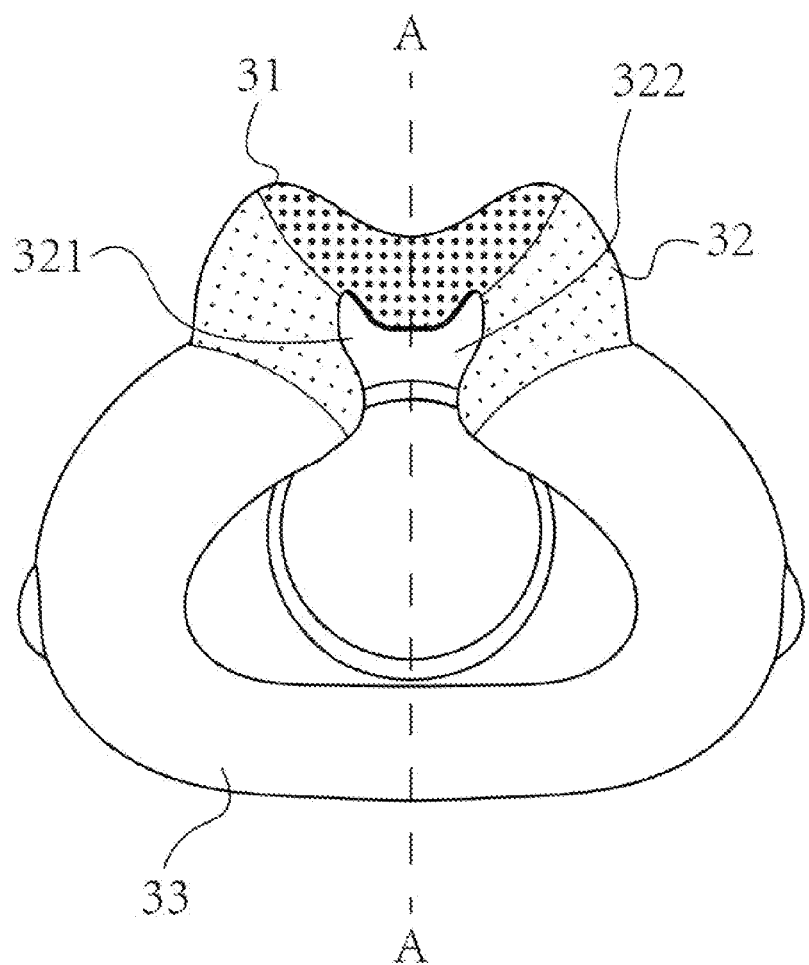
FIG. 2 is a schematic diagram of the structure of an oral and nasal sealing interface pad in another embodiment of the present disclosure from a different perspective.

Referring to FIG. 2, the lining pad 3 includes a nasal area corresponding to and abutting the user's nasal tip and a mouth area 33 corresponding to and surrounding the user's mouth. The space enclosed by the nasal area communicates with the space enclosed by the mouth area 33, forming an integrated respiratory chamber. The nasal area and the mouth area 33 together form an opening to accommodate the nose and mouth. That is to say, the oral and nasal sealing interface pad of this embodiment only includes an opening adjacent to the user's face, which communicates with both the user's nasal airway entrance and oral airway entrance, thereby avoiding the difficulty of processing multiple openings.

In an embodiment, as illustrated in FIGS. 1-8, the nasal area includes the nasal tip area 31 and the alar area 32 on both sides of the nasal tip area 31. The nasal tip area 31 corresponds to and contacts the user's nasal tip when worn, and the alar area 32 is located below the user's nasal tip and correspond to and contact the user's alae on both sides. The nasal tip area 31 has at least one thin area for accommodating the user's nasal tip, allowing the nasal tip area 31 to have sufficient deformation to contact the user's nasal tip, and the nasal tip area 31 has a first wing 34 for contacting the user's columella, which prevents the pressurized air from leaking when in contact with the user's columella. The alar area 32 has at least one non-thin area 38, and both sides of the alar area 32 are equipped with a second wing 35 for fitting the user's nasal base, with a straight-line distance of 10-15 mm between the second wings 35 on both sides. The non-thin area 38 in the alar area 32 provides a support portion 37 for the alar area 32 to prevent the collapse of the nasal area. Additionally, increasing the support portion 37 can better adapt to different nose shapes, and prevent the second wings 35 on both sides of the nasal area from being blown up by pressurized air. In this embodiment, the thickness of the thin area 36 is 0.3-1.2 mm, and the thin area 36 and adjacent non-thin area (that is, an area adjacent to and thicker than the thin area 36) can be smoothly connected (with a gradual transition) or abruptly connected (with the joint part forming a step). The thickness ratio between the thin area 36 and the non-thin area 38 is 0.05-0.8. Furthermore, the spring constant of the thin area is greater than that of the non-thin area, ensuring the support effect of the oral and nasal sealing interface pad 1 while allowing sufficient deformation of the nasal tip area 31 to accommodate the nasal tip and preventing collapse.

The spring constant (K) can be calculated using the formula K=F/X, where the unit is N/mm. In different locations of the oral and nasal sealing interface pad, a constant force (F) is applied vertically to measure the displacement (X) at the corresponding position, thereby obtaining the spring constant for that area. The spring constant range for the thin areas is 0.05-0.50 N/mm, while for the non-thin areas, the spring constant range is 0.11-1.5 N/mm.

Figure 4:
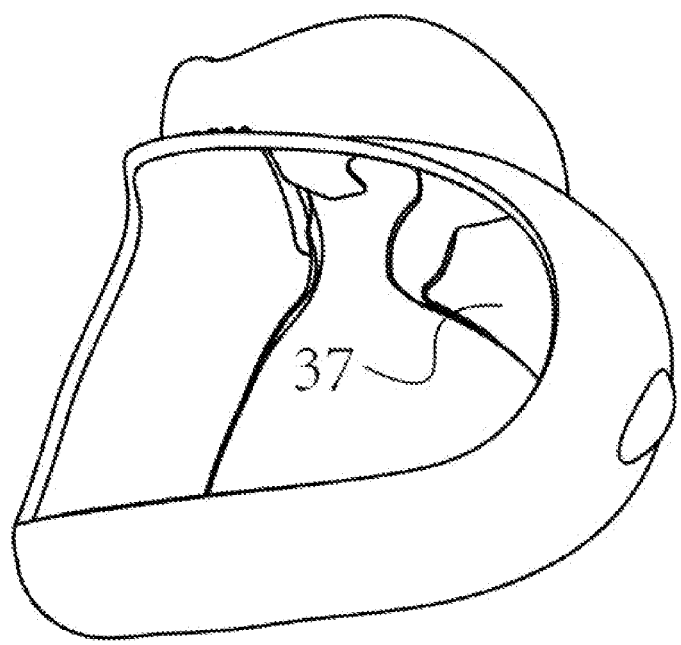
FIG. 4 is a schematic diagram of the structure of the lining pad in an embodiment of the present disclosure.
Figure 5:
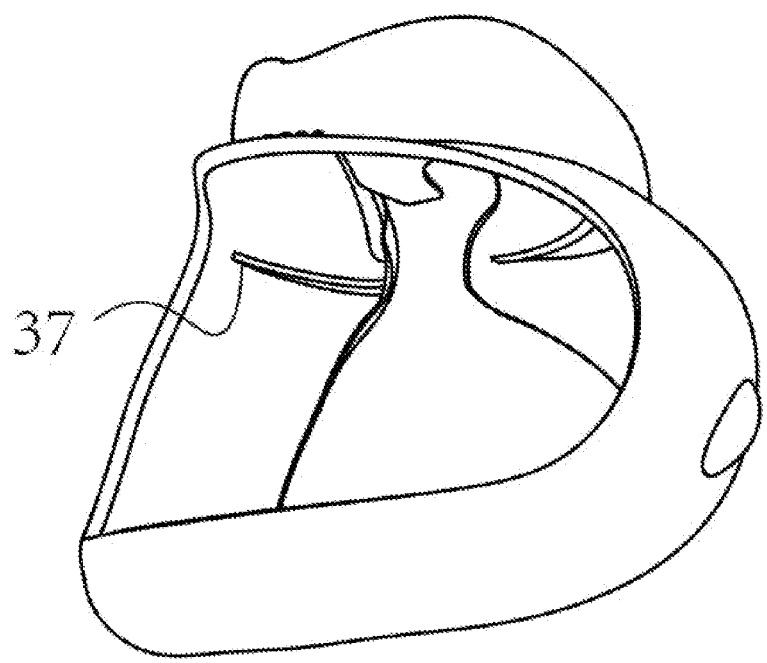
FIG. 5 is a schematic diagram of the structure of the lining pad in another embodiment of the present disclosure.

In one embodiment, the non-thin area 38 of the alar area 32 has ribs or multi-layer walls (as shown in FIGS. 4 and 5), and the non-thin area 38 can also be composed of a material layer with a thickness greater than the thin area 36, that is, the non-thin area 38 has a thicker wall. The thickness of the ribs is greater than or equal to 0.3 mm to meet the support function of the non-thin area 38 of the alar area 32 for the oral and nasal sealing interface pad 1 and prevent the collapse of the nasal area of the oral and nasal sealing interface pad and air leakage from the interface pad 1. In this embodiment, the opening edge of the nasal area has an irregular three-dimensional shape, for example, the enclosed space of the nasal area is an M-shaped or heart-shaped structure.

Figure 6:
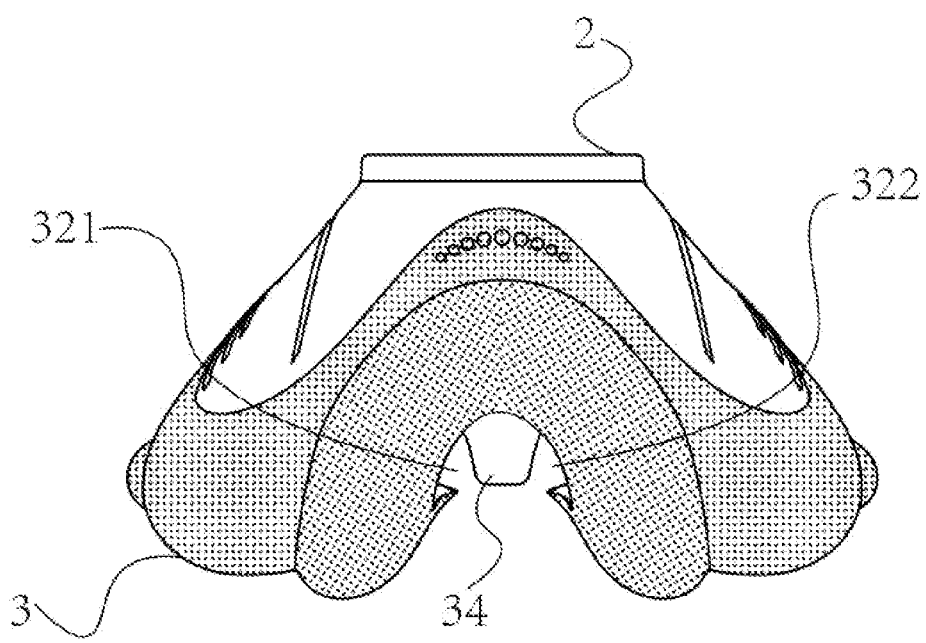
FIG. 6 is a schematic diagram of the structure of an oral and nasal sealing interface pad in an embodiment of the present disclosure from yet another perspective.

Although the physiological structure of the nose is the same for all races, the matching nasal shapes vary greatly due to different face shapes, facial proportions, head-body proportions, and body shapes, making the opening size of the nasal area extremely important. Studies have shown that the width of the alae in the general population is basically one-fifth of the facial width, which is about 20-30 mm. In this embodiment, the first wing 34 separates the alar area 32 on both sides to form the first opening 321 and the second opening 322 (as shown in FIG. 6). The distance between the first opening 321 and the second opening 322 can be at or between 10-30 mm. The straight-line distance between the second wings 35 on both sides is smaller than the distance between the first opening 321 and the second opening 322 to ensure the sealing effect of the oral-nasal sealing interface pad.

To prevent head movement from affecting the position of the interface pad during sleep, the lining pad 3 of the interface pad can be divided into different areas (as shown in FIG. 2), with the different areas having different friction coefficients. In this embodiment, the mouth area 33 includes the chin area and the cheek area, with the friction coefficient of the chin area being different from that of the cheek area to prevent the interface pad from falling off the chin when the user makes any movement of the mouth. Additionally, to ensure the stability of the first wing 34 in the nasal tip area 31, the friction coefficient of the outer surface of the first wing 34 is different from that of the other parts of the nasal area (the parts excluding the first wing 34 in the alar area 32 and nasal tip area 31) to prevent the first wing 34 from sliding due to oil and sweat being on the nasal tip, ensuring the seal of the interface pad. In this implementation (as shown in FIG. 1), the difference of the friction coefficient of the outer surface of the first wing 34 and the chin area from the friction coefficient of other parts of the nasal area and that of the cheek area is achieved through surface treatments (such as polishing) or later adding facial adhesives. Therefore, the outer surface of the first wing 34 has a smooth textured surface that visually distinguishes the first wing from the other parts in the nasal area (that is, it is easier to see the inside of the interface pad through the first wing).

Different parts of the oral and nasal sealing interface pad have different friction coefficients ($\mu$). The friction coefficient is expressed as $\mu=Ff/Fn$, where Ff is the frictional force, and Fn is the normal force. The measurement method is to test different parts of the oral and nasal interface pad under a load of 1.96N, at a rate of 30 millimeters per minute, in an environment of 37-39° C. on a glass substrate. The size of the force is measured and the friction coefficient is calculated based on the equation. The friction coefficient of the first wing and the chin area ranges from 0.25 to 1.7, while the friction coefficient for the remaining parts of the nasal area and the cheek area ranges from 0.3 to 2.5.

Figure 3:
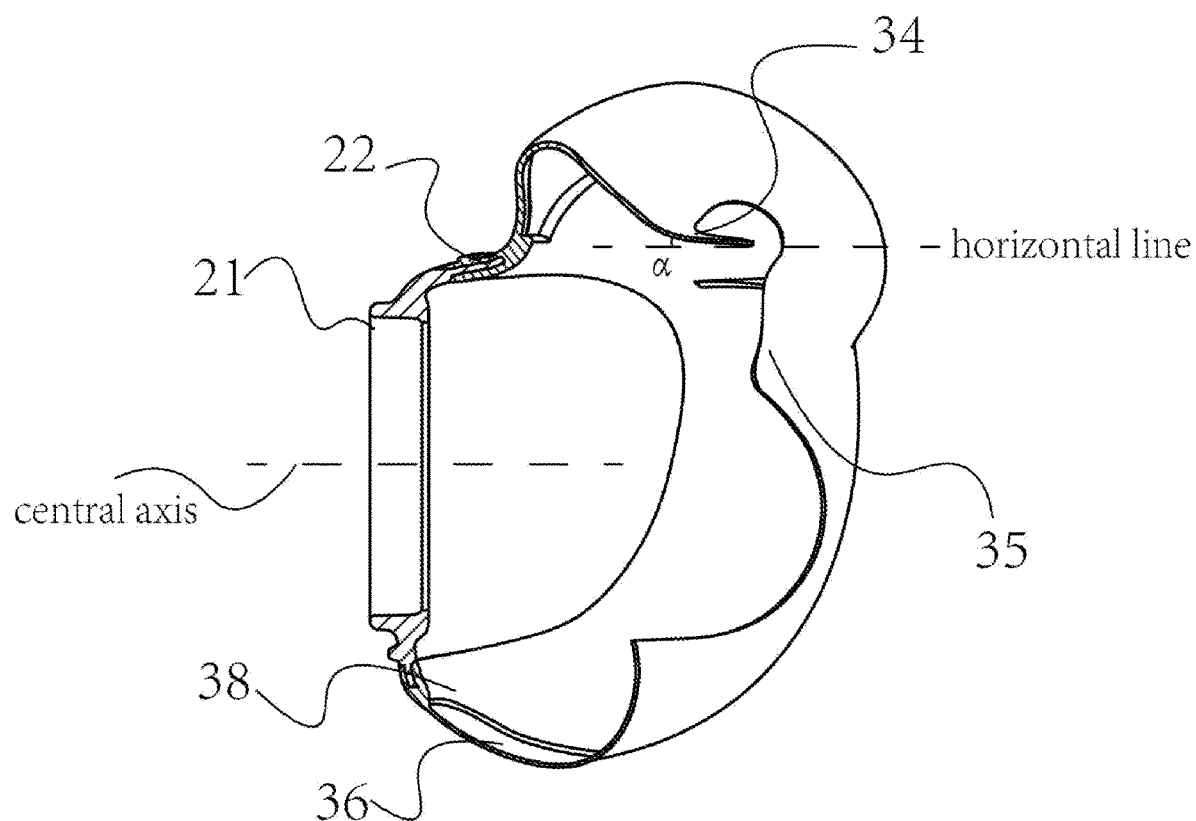
FIG. 3 is a cross-sectional schematic diagram of the A-A direction in the embodiment shown in FIG. 2.

Referring to FIG. 3, to allow the first wing 34 to perfectly fit the user's columella, when the axial direction of the circular opening 21 of the rigid part 2 is parallel to the horizontal line, the angle $\alpha$ between the first wing 34 and the horizontal line is 0-90°. In a further preferred embodiment, when the axial direction of the circular opening 21 of the rigid part 2 is parallel to the horizontal line, the first wing 34 is parallel to the horizontal line, making the first wing 34 approximately conform to the curvature of the user's columella.

For better fitting, the thickness of the first wing 34 is designed to be inflated or blown up under pressurized air to fit the user's columella. In this embodiment, the first wing 34 can swing relative to the nasal tip area 31 to provide conditions and possibilities for the first wing 34 to be inflated or blown up by pressurized air. Furthermore, to prevent the first wing 34 from being flipped over due to its thinness, the thickness of the first wing 34 can be at or between 0.3-1.2 mm. Referring to FIG. 6, the first wing 34 is smoothly connected to the edge of the nasal tip area 31, gradually decreasing in size, and its shape is approximately trapezoidal. For comfort considerations, the edge of the lining pad 3 has an arcuate portion to reduce the pressure of the lining pad 3 edge on the user's face. In this embodiment, the shape of the first wing 34 is adapted to the shape of the user's columella. For example, the shape of the first wing 34 can be an arc, an ellipse, or other shapes suitable for the user's columella. As seen in FIG. 3, the vertical cross-section of the connection between the first wing 34 and the nasal tip area 31 is an L-shaped structure to fit the contour of the user's columella.

For the general population, the length of the columella is approximately 10-30 mm, and the width is 4-10 mm. In this embodiment, to prevent the first wing 34 from being blown over or not touching the columella, as well as to prevent nasal obstruction and breathing difficulties caused by the first wing 34 being too long or too wide, the length of the first wing 34 can be at or between 2-20 mm, and the width of the first wing 34 can be at or between 2-20 mm.

Furthermore, it should be emphasized that to ensure the integrity of the lining pad 3 structure, the lining pad 3 is integrally formed through mold injection molding, which improves the stability and reliability of the connections between various parts. The lining pad 3 can be a single-layer wall structure or a multi-layer wall structure to meet the thickness requirements of the lining pad 3 for different facial conditions of different populations.

Additionally, in other embodiments, a thin area 36 can also be set in the chin area of the lining pad 3, so that when wearing the interface pad, the chin area of the lining pad 3 can adapt to the chin contours of different users through deformation.

The following describes several structures of the oral and nasal sealing interface pad of the present disclosure in conjunction with specific examples.

Embodiment 1

The oral and nasal sealing interface pad 1 in this embodiment is configured to provide positive pressure breathing gas to the user's airway and includes a rigid part 2 and a lining pad 3. One side of the rigid part 2 has a circular opening 21 for connecting to the positive pressure breathing gas, and the other side of the rigid part 2 has a joint part 22. The lining pad 3 is fixedly connected to the joint part 22 and is constructed to be positioned below the user's nose for delivering positive pressure breathing gas to the user's mouth and nasal airways. The lining pad 3 includes a nasal area corresponding to and abutting the user's nasal tip and a mouth area 33 corresponding to and surrounding the user's mouth. The space enclosed by the nasal area communicates with the space enclosed by the mouth area 33 and together form an integral respiratory chamber. The nasal area includes a nasal tip area 31 and alar area 32 on both sides of the nasal tip area 31. The nasal tip area 31 has at least one thin area for accommodating the user's nasal tip, and the nasal tip area 31 has a first wing 34 for contacting the user's columella. The alar area 32 has at least one non-thin area 38.

In the above embodiment, the non-thin area 38 of the alar area 32 is provided with ribs or multi-layer walls, and the thickness of the ribs is greater than or equal to 0.3 mm. The space enclosed by the nasal area can have an M-shaped structure or a heart-shaped structure. The first wing 34 separates the two sides of the alar area 32, forming a first opening 321 and a second opening 322, with the distance between the first opening 321 and the second opening 322 can be at or between 10-30 mm. Both sides of the alar area 32 are respectively provided with a second wing 35 for fitting the user's nasal tip, and the straight-line distance between the two second wings 35 can be at or between 10-15 mm, with the straight-line distance between the two second wings 35 being smaller than the distance between the first opening 321 and the second opening 322.

Embodiment 2

In this embodiment, the oral and nasal sealing interface pad 1 is configured to provide positive pressure breathing gas to the user's airway, including rigid part 2 and lining pad 3. One side of the rigid part 2 has a circular opening 21 for accessing positive pressure breathing gas, and the other side of the rigid part 2 has a joint part 22. The lining pad 3 is fixedly connected to the joint part 22 and is constructed to be located under the user's nose, for delivering the positive pressure breathing gas to the user's mouth and nasal airway. The lining pad 3 includes a nasal area corresponding to and abutting the user's nasal tip and a mouth area 33 corresponding to and surrounding the user's mouth. The space enclosed by the nasal area communicates with the space enclosed by the mouth area 33, forming an integral respiratory chamber. The nasal area includes a nasal tip area 31 and an alar area 32 on both sides of the nasal tip area 31. The nasal tip area 31 has at least one thin area for accommodating the user's nasal tip, and the nasal tip area 31 is provided with a first wing 34 for abutting the user's columella. In addition, in this embodiment, the first wing 34 has at least one of the following features:

The length of the first wing 34 can be at or between 2-20 mm;

The width of the first wing 34 can be at or between 2-20 mm;

The thickness of the first wing 34 can be at or between 0.3-1.2 mm;

When the axis direction of the circular opening 21 of the rigid part 2 is parallel to the horizontal line, the angle α between the first wing 34 and the horizontal line can be at or between 0-90°.

That is, the length of the first wing 34 can be at or between 2-20 mm; and/or the width of the first wing 34 can be at or between 2-20 mm; and/or the thickness of the first wing 34 can be at or between 0.3-1.2 mm; and/or when the axis direction of the circular opening 21 of the rigid part 2 is parallel to the horizontal line, the angle α between the first wing 34 and the horizontal line can be at or between 0-90°.

In the above embodiment, when the axis direction of the circular opening 21 of the rigid part 2 is parallel to the horizontal line, the first wing 34 is parallel to the horizontal line. The shape of the first wing 34 adapts to the shape of the user's columella; the vertical cross-section where the first wing 34 connects to the nasal tip area 31 has an L-shaped structure; the first wing 34 can swing relative to the nasal tip area 31.

Embodiment 3

In this embodiment, the oral and nasal sealing interface pad 1 is configured to provide positive pressure breathing gas to the user's airway, including rigid part 2 and lining pad 3. One side of the rigid part 2 has a circular opening 21 for accessing positive pressure breathing gas, and the other side of the rigid part 2 has a joint part 22. The lining pad 3 is fixedly connected to the joint part 22 and is constructed to be located under the user's nose, for delivering the positive pressure breathing gas to the user's mouth and nasal airway. The lining pad 3 includes a nasal area corresponding to and abutting the user's nasal tip and a mouth area 33 corresponding to and surrounding the user's mouth. The space enclosed by the nasal area communicates with the space enclosed by the mouth area 33, forming an integral respiratory chamber. The nasal area includes a nasal tip area 31 and an alar area 32 on both sides of the nasal tip area 31. The nasal tip area 31 has at least one thin area for accommodating the user's nasal tip, and the nasal tip area 31 is provided with a first wing 34 for abutting the user's columella.

In the above embodiment, the mouth area 33 includes a chin area and cheek area, and the friction coefficient of the chin area is different from the friction coefficient of the cheek area.

Embodiment 4

In this embodiment, the oral and nasal sealing interface pad 1 is configured to provide positive pressure breathing gas to the user's airway, including rigid part 2 and lining pad 3. One side of the rigid part 2 has a circular opening 21 for accessing positive pressure breathing gas, and the other side of the rigid part 2 has a joint part 22. The lining pad 3 is fixedly connected to the joint part 22 and is constructed to be located under the user's nose, for delivering the positive pressure breathing gas to the user's mouth and nasal airway. The lining pad 3 includes a nasal area corresponding to and abutting the user's nasal tip and a mouth area 33 corresponding to and surrounding the user's mouth. The space enclosed by the nasal area communicates with the space enclosed by the mouth area 33, forming an integral respiratory chamber. The nasal area includes a nasal tip area 31 and an alar area 32 on both sides of the nasal tip area 31. The nasal tip area 31 has at least one thin area for accommodating the user's nasal tip, the thickness of the thin area can be at or between 0.3-1.2 mm, and the thickness ratio of the thin area to the adjacent non-thin area 38 is 0.05-0.8.

In the above embodiment, the spring constant of the thin area 36 is greater than the spring constant of the adjacent non-thin area 38. The hardness of the rigid part 2 is greater than the hardness of the lining pad 3, the lining pad 3 is made of silicone material, and the edge of the lining pad 3 has an arcuate portion. The lining pad 3 is integrally formed and is a single-layer wall structure or multi-layer wall structure.

Furthermore, according to the needs, the technical features in the above embodiments can be combined to obtain an oral and nasal sealing interface pad including all or part of the above technical features.

The oral and nasal sealing interface pad 1 of the present disclosure has at least the following beneficial effects:

The strap connecting the nasal area and the mouth area 33 is removed, the space enclosed by the nasal area communicates with the space enclosed by the mouth area 33, forming an integral respiratory chamber. The alar area 32 on both sides have a larger deformation space, which can adapt to the user's alae and nasal base curvature. The removal of the strap is beneficial for the mask to fit the facial contour on both sides under the treatment pressure. The non-thin area 38 setting in the alar area 32 ensures that the interface pad is sealed with the face while effectively preventing the alar area 32 from deforming outward.

The strap connecting the nasal area and the mouth area 33 is removed, and the side of the interface pad facing the user's face has only one opening (the space enclosed by the nasal area communicates with the space enclosed by the mouth area 33), which is larger and facilitates the removal of the mold inside the interface pad during the processing. The removal of the strap not only achieves a good sealing effect but also simplifies the product structure, facilitates production, improves efficiency, and reduces costs.

When using the interface pad, it is worn from bottom to top, allowing the nasal tip to fit just right with the nasal tip area 31 of the interface pad. Only the nose and mouth need to be accommodated within a single respiratory chamber, without tedious adjustments to place the nose and mouth within the corresponding area range, making it easy to wear the interface pad and reducing the difficulty of wearing it.

By increasing the friction coefficient of the outer surface of the first wing 34, the friction force between the first wing 34 and the skin is increased, making it less likely for the first wing 34 to shift during the wearing process, due to airflow pressure or user movement. This ensures the sealing performance when the interface pad is worn.

ASPECTS

Aspect 1: An oral and nasal sealing interface pad, configured to provide positive pressure breathing gas to a user's airway, the oral and nasal sealing interface pad comprising: a rigid part, one side of which has a circular opening for connecting positive pressure breathing gas, and another side of the rigid part having a joint part; and a lining pad, which is fixedly connected to the joint part and constructed to be located below a user's nose, for delivering positive pressure breathing gas to a user's mouth and nasal airways, the lining pad including a nasal area corresponding to and configured to abut a user's nasal tip and a mouth area corresponding to and surrounding the user's mouth, and a space enclosed by the nasal area being connected to a space enclosed by the mouth area, together forming an integrated respiratory chamber, wherein the nasal area includes a nasal tip area and an alar area on two sides of the nasal tip area, the nasal tip area having at least one thin area for accommodating the user's nasal tip and being equipped with a first wing for abutting against a user's columella, and the alar area having at least one non-thin area thicker than the thin area in the nasal tip area.

Aspect 2: The oral and nasal sealing interface pad according to Aspect 1, wherein the non-thin area of the alar area is provided with ribs or multi-layer walls, a thickness of the ribs being greater than or equal to 0.3 mm.

Aspect 3: The oral and nasal sealing interface pad according to any of Aspects 1-2, wherein the space enclosed by the nasal area has an M-shaped structure or a heart-shaped structure.

Aspect 4: The oral and nasal sealing interface pad according to any of Aspects 1-3, wherein a thickness of the thin area in the nasal tip area is 0.3-1.2 mm.

Aspect 5: The oral and nasal sealing interface pad according to any of Aspects 1-4, wherein the first wing separates the two sides of the alar area to form a first opening and a second opening, a distance between the first opening and the second opening being at most 30 mm.

Aspect 6: The oral and nasal sealing interface pad according to Aspect 5, wherein the two sides of the alar area are provided with a second wing for fitting a user's nasal base, a straight-line distance between the two second wings being at or between 10-15 mm, and the straight-line distance between the two second wings is less than the distance between the first opening and the second opening.

Aspect 7: An oral and nasal sealing interface pad, configured to provide positive pressure breathing gas to a user's airway, the oral and nasal sealing interface pad comprising: a rigid part, one side of which has a circular opening for connecting positive pressure breathing gas, and another side of the rigid part has a joint part; and a lining pad, which is fixedly connected to the joint part and constructed to be located below a user's nose, for delivering positive pressure breathing gas to a user's mouth and nasal airways, the lining pad including a nasal area corresponding to and configured to abut a user's nasal tip and a mouth area corresponding to and surrounding the user's mouth, and a space enclosed by the nasal area being connected to a space enclosed by the mouth area, together forming an integrated respiratory chamber, wherein the nasal area includes a nasal tip area and an alar area on two sides of the nasal tip area, the nasal tip area having at least one thin area for accommodating the user's nasal tip, and the nasal tip area is equipped with a first wing for abutting against a user's columella, and wherein the first wing has at least one of the following features: a length of the first wing is at or between 2-20 mm; a width of the first wing is at or between 2-20 mm; a thickness of the first wing is at or between 0.3-1.2 mm; or when an axial direction of the circular opening of the rigid part is parallel to a horizontal line, an angle α between the first wing and the horizontal line is at or between 0-90°.

Aspect 8: The oral and nasal sealing interface pad according to Aspect 7, wherein when the axial direction of the circular opening of the rigid part is parallel to the horizontal line, the first wing is parallel to the horizontal line.

Aspect 9: The oral and nasal sealing interface pad according to any of Aspects 7-8, wherein a shape of the first wing is configured to adapt to the shape of the user's columella, and a vertical cross-section of the first wing connected to the nasal tip area has an L-shaped structure.

Aspect 10: The oral and nasal sealing interface pad according to Aspect 9, wherein the first wing is configured to swing relative to the nasal tip area.

Aspect 11: The oral and nasal sealing interface pad according to any of Aspects 7-10, wherein the lining pad is integrally formed.

Aspect 12: An oral and nasal sealing interface pad, configured to provide positive pressure breathing gas to a user's airway, the oral and nasal sealing interface pad comprising: a rigid part, one side of which has a circular opening for connecting positive pressure breathing gas, and another side of the rigid part has a joint part; and a lining pad, which is fixedly connected to the joint part and constructed to be located below a user's nose, for delivering positive pressure breathing gas to a user's mouth and nasal airways, the lining pad includes a nasal area corresponding to and configured to abut a user's nasal tip and a mouth area corresponding to and surrounding the user's mouth, and a space enclosed by the nasal area being connected to a space enclosed by the mouth area, together forming an integrated respiratory chamber, wherein the nasal area includes a nasal tip area and an alar area on two sides of the nasal tip area, the nasal tip area having at least one thin area for accommodating the user's nasal tip, and the nasal tip area is equipped with a first wing for abutting against a user's columella.

Aspect 13: The oral and nasal sealing interface pad according to Aspect 12, wherein the mouth area includes a chin area and a cheek area, and a friction coefficient of the chin area is different from a friction coefficient of the cheek area.

Aspect 14: The oral and nasal sealing interface pad according to any of Aspects 12-13, wherein a thickness of the first wing is 0.3-1.2 mm.

Aspect 15: The oral and nasal sealing interface pad according to any of Aspects 12-14, wherein an outer surface of the first wing that visually distinguishes the first wing from the other parts in the nasal area.

Aspect 16: An oral and nasal sealing interface pad, configured to provide positive pressure breathing gas to a user's airway, the oral and nasal sealing interface pad comprising: a rigid part, one side of which has a circular opening for connecting positive pressure breathing gas, and another side of the rigid part has a joint part; and a lining pad, which is fixedly connected to the joint part and constructed to be located below a user's nose, for delivering positive pressure breathing gas to a user's mouth and nasal airways, the lining pad including a nasal area corresponding to and configured to abut a user's nasal tip and a mouth area corresponding to and surrounding the user's mouth, and a space enclosed by the nasal area is connected to a space enclosed by the mouth area, together forming an integrated respiratory chamber, wherein the nasal area includes a nasal tip area and an alar area on two sides of the nasal tip area, the nasal tip area having at least one thin area for accommodating the user's nasal tip, a thickness of the thin area being at or between 0.3-1.2 mm, and a thickness ratio between the thin area and an adjacent non-thin area being at or between 0.05-0.8.

Aspect 17: The oral and nasal sealing interface pad according to Aspect 16, wherein a spring constant of the thin area is greater than a spring constant of the adjacent non-thin area.

Aspect 18: The oral and nasal sealing interface pad according to any of Aspects 16-17, wherein a hardness of the rigid part is greater than a hardness of the lining pad, the lining pad being made of silicone material, and an edge of the lining pad is provided with an arcuate portion.

Aspect 19: The oral and nasal sealing interface pad according to any of Aspects 16-18, wherein the lining pad is integrally molded and the lining pad has a single-layer wall structure or a multi-layer wall structure.

Aspect 20: The oral and nasal sealing interface pad according to any of Aspects 16-19, wherein the lining pad is permanently attached to the rigid part.

The various technical features of the above-described embodiments can be combined in any way. For the sake of brevity, not all possible combinations of the various technical features in the above embodiments have been described. However, as long as these technical feature combinations do not conflict, they should be considered within the scope of this specification.

The above-described embodiments only express several implementation methods of the present disclosure, which are described in a more specific and detailed manner, but should not be construed as limiting the scope of the patent for the disclosure. It should be noted that, for those skilled in the art, without departing from the concept of the present disclosure, several modifications and improvements can also be made, which are all within the scope of protection of the present disclosure. Therefore, the scope of protection for the disclosure patent should be subject to the appended claims.

The invention claimed is:

1. An oral and nasal sealing interface pad, configured to provide positive pressure breathing gas to a user's airway, the oral and nasal sealing interface pad comprising:
    a rigid part, one side of which has a circular opening for connecting the positive pressure breathing gas, and another side of the rigid part having a joint part; and
    a lining pad, which is fixedly connected to the joint part and constructed to be located below a user's nose, for delivering the positive pressure breathing gas to a user's mouth and nasal airways, the lining pad including a nasal area corresponding to and configured to abut a user's nasal tip and a mouth area corresponding to and surrounding the user's mouth, and a space enclosed by the nasal area being connected to a space enclosed by the mouth area, together forming an integrated respiratory chamber,
    wherein the nasal area only includes a nasal tip area and an alar area on two sides of the nasal tip area, the nasal tip area having at least one thin area for accommodating the user's nasal tip and connected to a first wing for abutting against a user's columella, and the alar area having at least one non-thin area thicker than the thin area in the nasal tip area,
    wherein the first wing is connected to and extends only from an inner edge of the nasal tip area and has an outer surface having a friction coefficient greater than a friction coefficient of other parts of the nasal area, and
    wherein an axial direction of the circular opening of the rigid part is parallel to a horizontal line, and the first wing is parallel to the horizontal line such that the first wing is configured to be inflated when the positive pressure breathing gas is provided to the oral and nasal sealing interface pad such that the first wing abuts the user's columella.

2. The oral and nasal sealing interface pad according to claim 1, wherein the non-thin area of the alar area is provided with ribs or multi-layer walls, a thickness of the ribs being greater than or equal to 0.3 mm.

3. The oral and nasal sealing interface pad according to claim 1, wherein the space enclosed by the nasal area has an M-shaped structure or a heart-shaped structure.

4. The oral and nasal sealing interface pad according to claim 1, wherein a thickness of the thin area in the nasal tip area is 0.3-1.2 mm.

5. The oral and nasal sealing interface pad according to claim 1, wherein the first wing separates the two sides of the alar area to form a first opening and a second opening, a distance between the first opening and the second opening being at most 30 mm.

6. The oral and nasal sealing interface pad according to claim 5, wherein the two sides of the alar area are each provided with a second wing for fitting a user's nasal base, a straight-line distance between the two second wings being at or between 10-15 mm, and the straight-line distance between the two second wings is less than the distance between the first opening and the second opening.

7. The oral and nasal sealing interface pad according to claim 1, wherein the first wing is formed entirely of silicone.

8. An oral and nasal sealing interface pad, configured to provide positive pressure breathing gas to a user's airway, the oral and nasal sealing interface pad comprising:
a rigid part, one side of which has a circular opening for connecting the positive pressure breathing gas, and another side of the rigid part has a joint part; and
a lining pad, which is fixedly connected to the joint part and constructed to be located below a user's nose, for delivering the positive pressure breathing gas to a user's mouth and nasal airways, the lining pad including a nasal area corresponding to and configured to abut a user's nasal tip and a mouth area corresponding to and surrounding the user's mouth, and a space enclosed by the nasal area being connected to a space enclosed by the mouth area, together forming an integrated respiratory chamber,
wherein the nasal area only includes a nasal tip area and an alar area on two sides of the nasal tip area, the nasal tip area having at least one thin area for accommodating the user's nasal tip, and the nasal tip area is connected to a first wing for abutting against a user's columella,
wherein the first wing is connected to and extends only from an inner edge of the nasal tip area, wherein an axial direction of the circular opening of the rigid part is parallel to a horizontal line, and the first wing is parallel to the horizontal line such that the first wing is configured to be inflated when the positive pressure breathing gas is provided to the oral and nasal sealing interface pad such that the first wing abuts the user's columella, and
wherein the first wing has at least one of the following features:
a length of the first wing is at or between 2-20 mm;
a width of the first wing is at or between 2-20 mm; or
a thickness of the first wing is at or between 0.3-1.2 mm, and
wherein the first wing has an outer surface having a friction coefficient greater than a friction coefficient of other parts of the nasal area.

9. The oral and nasal sealing interface pad according to claim 8, wherein a shape of the first wing is configured to adapt to the shape of the user's columella, and a vertical cross-section of the first wing connected to the nasal tip area has an L-shaped structure.

10. The oral and nasal sealing interface pad according to claim 8, wherein the lining pad is integrally formed.

11. An oral and nasal sealing interface pad, configured to provide positive pressure breathing gas to a user's airway, the oral and nasal sealing interface pad comprising:
a rigid part, one side of which has a circular opening for connecting the positive pressure breathing gas, and another side of the rigid part has a joint part; and
a lining pad, which is fixedly connected to the joint part and constructed to be located below a user's nose, for delivering the positive pressure breathing gas to a user's mouth and nasal airways, the lining pad includes a nasal area corresponding to and configured to abut a user's nasal tip and a mouth area corresponding to and surrounding the user's mouth, and a space enclosed by the nasal area being connected to a space enclosed by the mouth area, together forming an integrated respiratory chamber,
wherein the nasal area only includes a nasal tip area and an alar area on two sides of the nasal tip area, the nasal tip area having at least one thin area for accommodating the user's nasal tip, and the nasal tip area is connected to a first wing for abutting against a user's columella,
wherein the first wing is connected to and extends only from an inner edge of the nasal tip area and has an outer surface having a friction coefficient greater than a friction coefficient of other parts of the nasal area, and
wherein an axial direction of the circular opening of the rigid part is parallel to a horizontal line, and the first wing is parallel to the horizontal line such that the first wing is configured to be inflated when the positive pressure breathing gas is provided to the oral and nasal sealing interface pad such that the first wing abuts the user's columella.

12. The oral and nasal sealing interface pad according to claim 11, wherein the mouth area includes a chin area and a cheek area, and a friction coefficient of the chin area is different from a friction coefficient of the cheek area.

13. The oral and nasal sealing interface pad according to claim 11, wherein a thickness of the first wing is 0.3-1.2 mm.

14. The oral and nasal sealing interface pad according to claim 11, wherein an outer surface of the first wing visually distinguishes the first wing from the other parts in the nasal area.

15. An oral and nasal sealing interface pad, configured to provide positive pressure breathing gas to a user's airway, the oral and nasal sealing interface pad comprising:
a rigid part, one side of which has a circular opening for connecting the positive pressure breathing gas, and another side of the rigid part has a joint part; and
a lining pad, which is fixedly connected to the joint part and constructed to be located below a user's nose, for delivering the positive pressure breathing gas to a user's mouth and nasal airways, the lining pad including a nasal area corresponding to and configured to abut a user's nasal tip and a mouth area corresponding to and surrounding the user's mouth, and a space enclosed by the nasal area is connected to a space enclosed by the mouth area, together forming an integrated respiratory chamber,
wherein the nasal area only includes a nasal tip area and an alar area on two sides of the nasal tip area, the nasal tip area having at least one thin area for accommodating the user's nasal tip and connected to a first wing for abutting against a user's columella, a thickness of the thin area being at or between 0.3-1.2 mm, and a thickness ratio between the thin area and an adjacent non-thin area being at or between 0.05-0.8, wherein the first wing is connected to and extends only from an inner edge of the nasal tip area and has an outer surface having a friction coefficient greater than a friction coefficient of other parts of the nasal area, and wherein an axial direction of the circular opening of the rigid part is parallel to a horizontal line, and the first wing is parallel to the horizontal line such that the first wing is configured to be inflated when the positive pressure breathing gas is provided to the oral and nasal sealing interface pad such that the first wing abuts the user's columella.

16. The oral and nasal sealing interface pad according to claim 15, wherein a spring constant of the thin area is greater than a spring constant of the adjacent non-thin area.

17. The oral and nasal sealing interface pad according to claim 15, wherein a hardness of the rigid part is greater than a hardness of the lining pad, the lining pad being made of silicone material, and an edge of the lining pad is provided with an arcuate portion.

18. The oral and nasal sealing interface pad according to claim 15, wherein the lining pad is integrally molded and the lining pad has a single-layer wall structure or a multi-layer wall structure.

19. The oral and nasal sealing interface pad according to claim 15, wherein the lining pad is permanently attached to the rigid part.

* * * * *